(12) United States Patent
Shah et al.

(10) Patent No.: US 6,562,033 B2
(45) Date of Patent: May 13, 2003

(54) INTRADISCAL LESIONING APPARATUS

(75) Inventors: Krishan Shah, Mississauga (CA);
Frank Headley Baylis, Beaconsfield (CA); Mark Leung, Markham (CA)

(73) Assignee: Baylis Medical Co., Montreal (CA)

( * ) Notice: Subject to any disclaimer, the term of this patent is extended or adjusted under 35 U.S.C. 154(b) by 0 days.

(21) Appl. No.: 09/827,922

(22) Filed: Apr. 9, 2001

(65) Prior Publication Data

US 2002/0147444 A1 Oct. 10, 2002

(51) Int. Cl.$^7$ .............................................. A61B 18/18
(52) U.S. Cl. ........................... 606/41; 607/117; 606/46
(58) Field of Search .................. 606/34, 41, 42, 606/45–50, 28; 607/101, 102, 117, 118; 604/95.05

(56) References Cited

U.S. PATENT DOCUMENTS

| | | | | |
|---|---|---|---|---|
| 5,167,658 A | * | 12/1992 | Ensslin | ........................ 606/34 |
| 5,201,729 A | | 4/1993 | Hertzmann et al. | |
| 5,433,739 A | | 7/1995 | Sluijter et al. | |
| 5,980,504 A | | 11/1999 | Sharkey et al. | |
| 6,007,570 A | | 12/1999 | Sharkey et al. | |
| 6,073,051 A | | 6/2000 | Sharkey et al. | |
| 6,095,149 A | | 8/2000 | Sharkey et al. | |
| 6,099,514 A | | 8/2000 | Sharkey et al. | |
| 6,122,549 A | | 9/2000 | Sharkey et al. | |
| 6,126,682 A | | 10/2000 | Sharkey et al. | |
| 6,258,086 B1 | * | 7/2001 | Ashley et al. | ................. 606/41 |

FOREIGN PATENT DOCUMENTS

WO    WO99/47058 A2    9/1999

OTHER PUBLICATIONS

Michael Karasek, MD, and Nikolai Bogduk, MD, PhD, DSct, "Twelve–Month Follow–Up of a Controlled Trial of Intradiscal Thermal Anuloplasty for Back Pain Due to Internal Disc Disruption", Reprinted from Spine, vol. 25, No. 20, Oct. 2000, Lippincott Williams & Wilkins, pp. 2601–2607.

Jeffrey A. Saal, MD, and Joel S. Saal, MD, "Intradiscal Electrothermal Therapy for the Treatment of Chronic Discogenic Low Back Pain", Operative Techniques in Orthopaedics, vol. 10, No. 4, Oct. 2000, pp. 271–281.

IDET Reference Literature List with abstracts, Mar. 15, 2001, Oratec Interventions Inc., 77 0023, Rev. 09, pp. 1–5.

IDET Procedure with Spine CATCH, Dec. 2000, Oratec Interventions Inc., 77 0004, Rev. 4, pp. 1–6.

http://www.orthoassociates.com/IDET.htm, Jun. 11, 2000, 5 pages.

(List continued on next page.)

Primary Examiner—Michael Peffley
(74) Attorney, Agent, or Firm—Ogilvy Renault

(57) ABSTRACT

An intradiscal lesioning device for percutaneous treatment of a patient's intervertebral disc. An elongate introducer having a longitudinal hollow bore is surgically inserted from the patient's skin to extend through the annulus fibrosus thereby providing external surgical access to the nucleus pulposus through the introducer bore. An elongate probe slides through and flexibly conforms to the bore when longitudinally inserted through the bore of the introducer. The distal portion of the probe is capable of resiliently conforming to the bore in a longitudinally slidably confined configuration and resiliently rebounding to a deployed configuration when released within the nucleus pulposus. The distal portion houses lesioning devices for emitting energy toward the inner wall of the annulus fibrosus when the distal portion is in the deployed configuration. Examples of suitable energy sources include: thermal energy; radio frequency electric current; microwave emission; ultrasound emission; radioactive emission; and optical emission.

11 Claims, 14 Drawing Sheets

OTHER PUBLICATIONS

Derby, R., Eek, B., Chen, Y., O'Neill, C., Ryan D., Intradiscal Electrothermal Annuloplasty (IDET): A novel Approach for Treating Chronic Discogenic Back Pain. *Neuromodulation. 2000*, 3(2), 82–88.

Saal, Joel, Saal, Jeffrey. Management of Chronic Discogenic Low Back Pain with a Thermal Intradiscal Cathethe. *Spine*. 2000, 25(3), 382–388.

Wiesel S W, Sharp Criticism of Intradiscal Thermal Therapy Research. *The Back Letter*. 2000, 15(6), 61–64. Lippincott Williams & Wilkins, 1 page.

Wiesel, S.W., IDET: Is There Any Indication That Intradiscal Thermal Therapy Works? *The Back Letter*. 2000, 15(6), 64–65. Lippincott Williams & Wilkins, 3 pages.

IDET Reference Literature List, Jun. 15, 2000, Oratec Interventions Inc., Doc #770023 Rev 0S, 7 pages.

Abstract: Arthroscopic Electro–Thermal Surgery for Discogenic Low Back Pain: A preliminary Report. May 25, 1998, 1 page.

Press Release: Spine Journal Studies Support Oratec's IDET Back Pain Treatment Two Peer Reviewed Articles Report Substantial Reduction in Pain. Oratec, Oct. 19, 2000, 1 page.

510(k) Summary: SpineCATH Mar. 19, 1998 and Document #K974464, Jan. 23, 1998, 8 pages.

510(k) Summary SpineCATH, Dec. 17, 1999, Document No. K993967, 4 pages.

Yahoo News Re: Oratec Dec. 20, 2000, Jan. 25, 2001, Mar. 3, 2001, 6 pages.

510(k) Summary: Radionics Disc catheter Electrode System, Document K001741, Oct. 23, 2000, 5 pages.

SpineCATH Intradiscal catheter by Oratec, Instructions for use, Document No. 700242, Rev. 03,.

Radionics RF Lesioning Systems and RF Catheter Electrode System Photo.

Spine vol. 21, No. 15, HOUPT, Jonathan C. et al. Experimental Study of Temperature Distributions and Thermal Transport During Radiofrequency Current Therapy of the Intervertebral Disc. pp. 1808–1813, 1996, Lippincott–Raven Publishers.m by J.C. Houpt, Scanner, E. McFarland.

Nerve Ingrowth Into Diseased Intervertebral Disc in Chronic Back Pain, A.J. Freement, T.E. Peacock, P. Goupille, J.A. Hoyland, J. O'Brian, MIV Jayson., The Lancet, pp. 178–181.

* cited by examiner

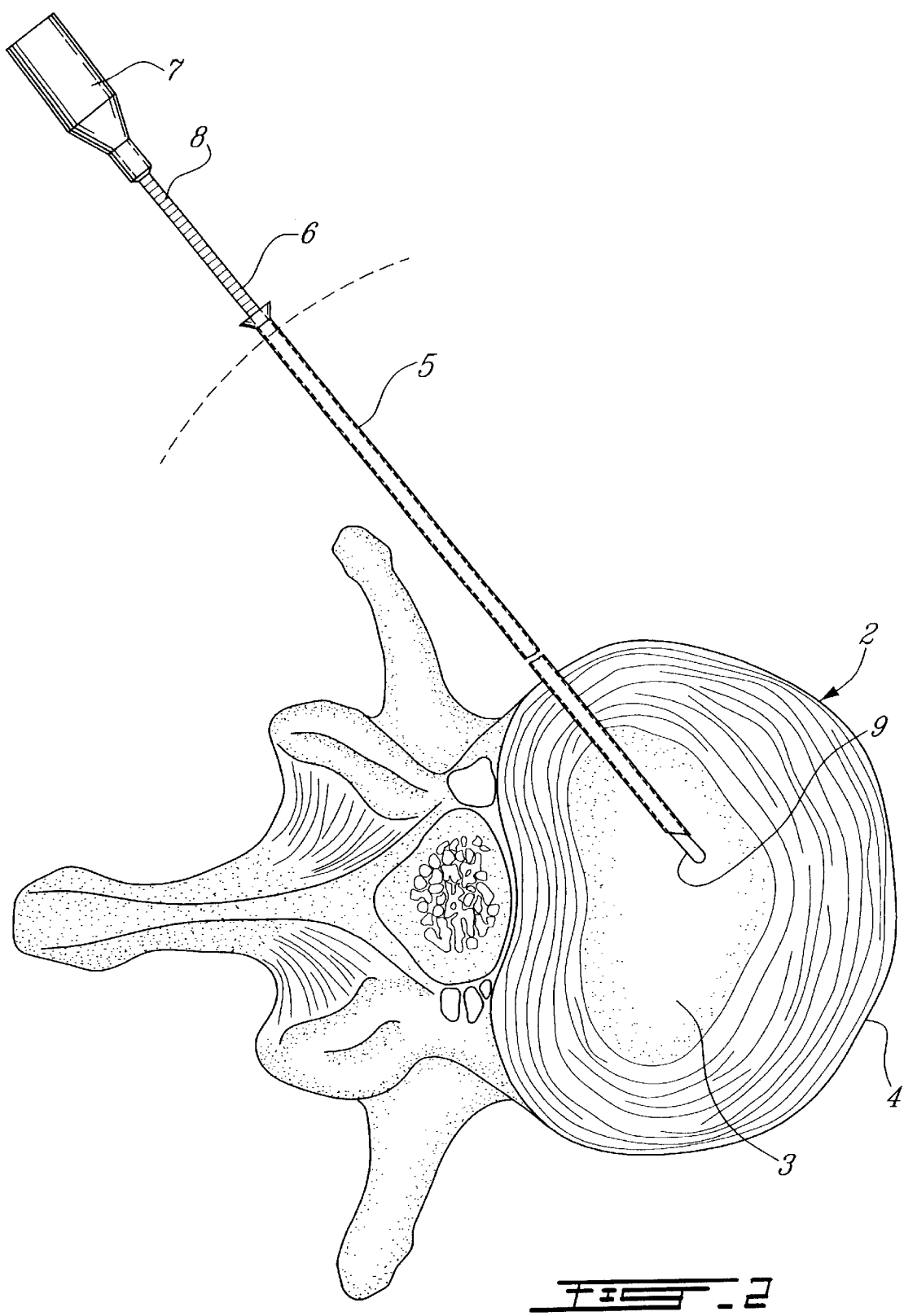

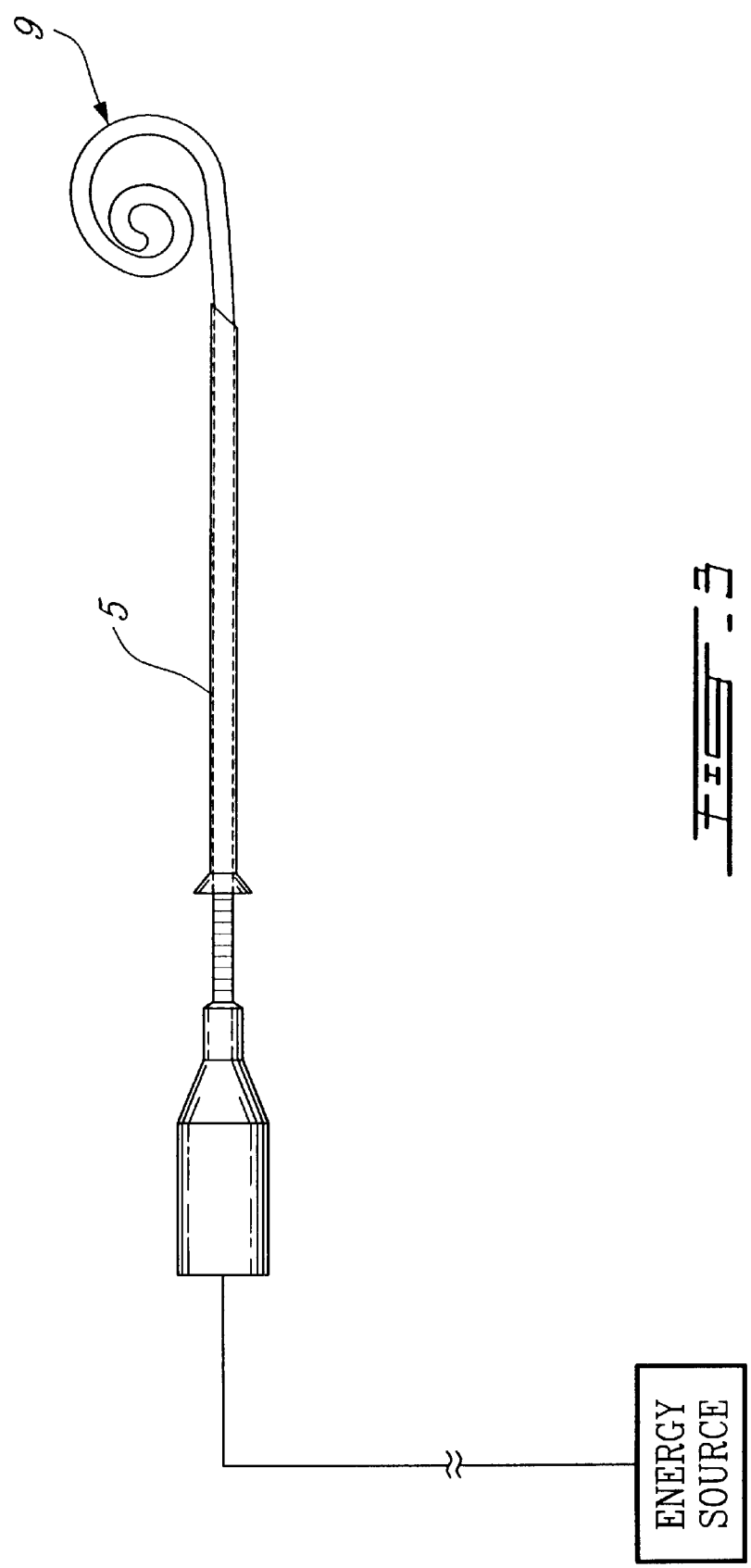

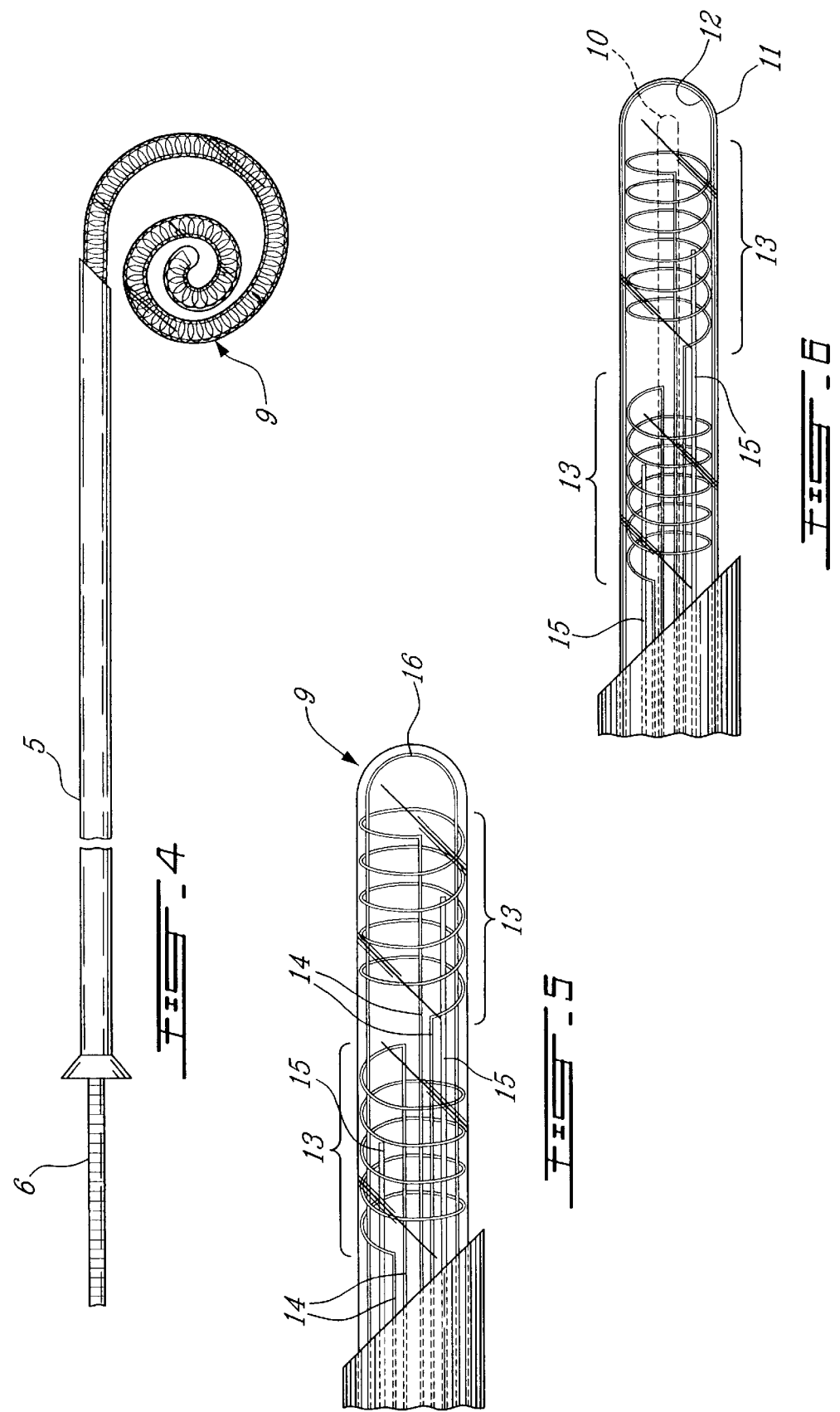

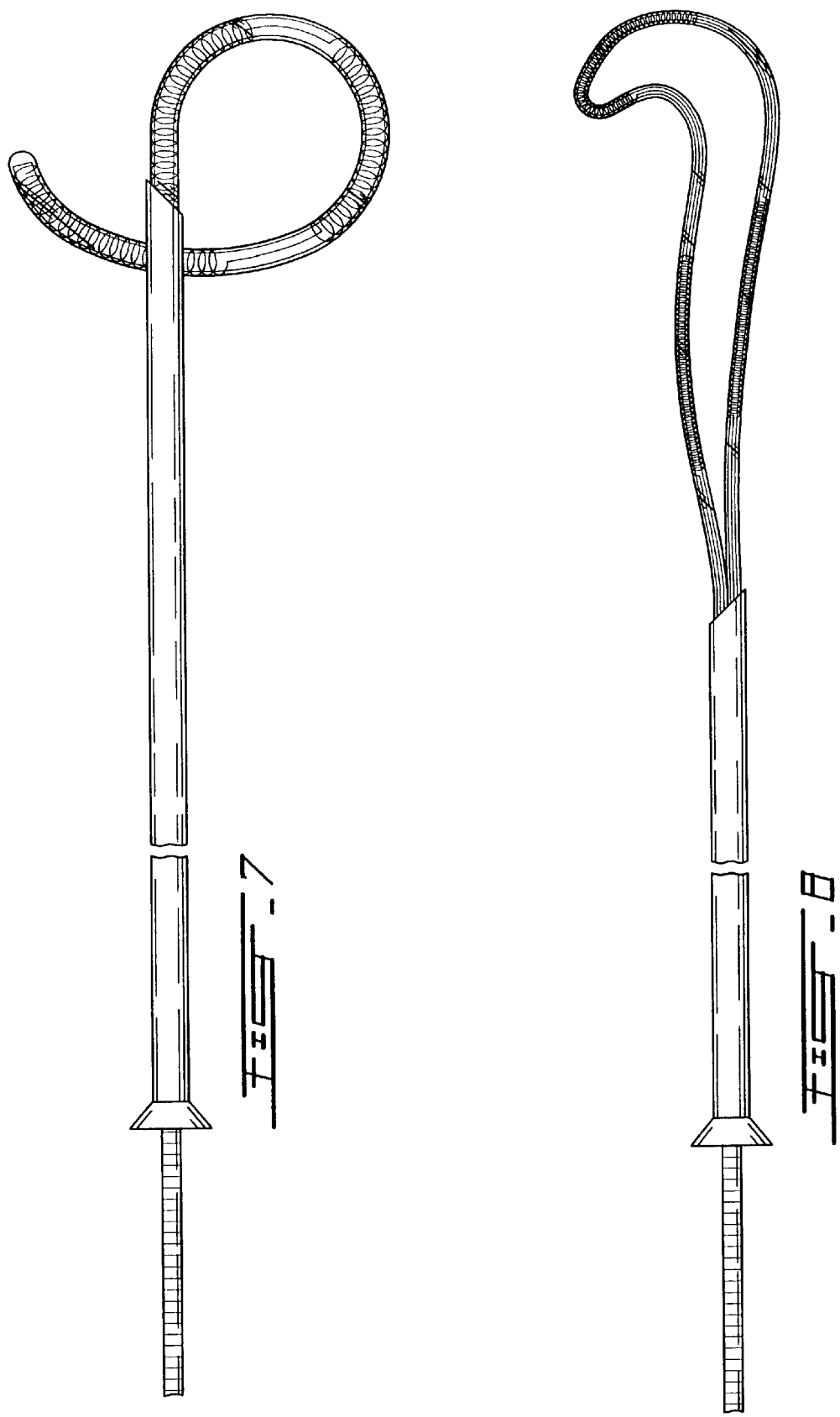

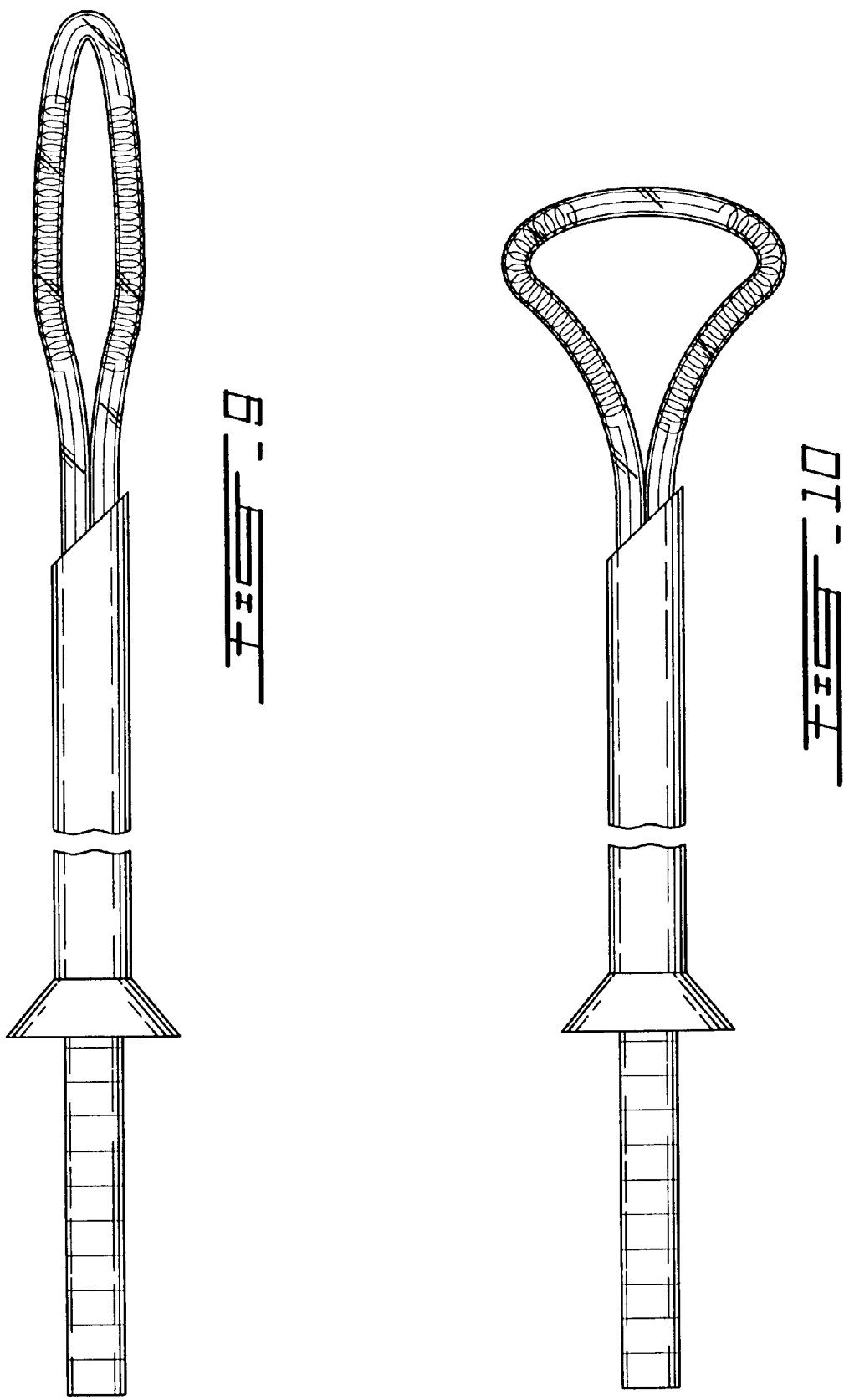

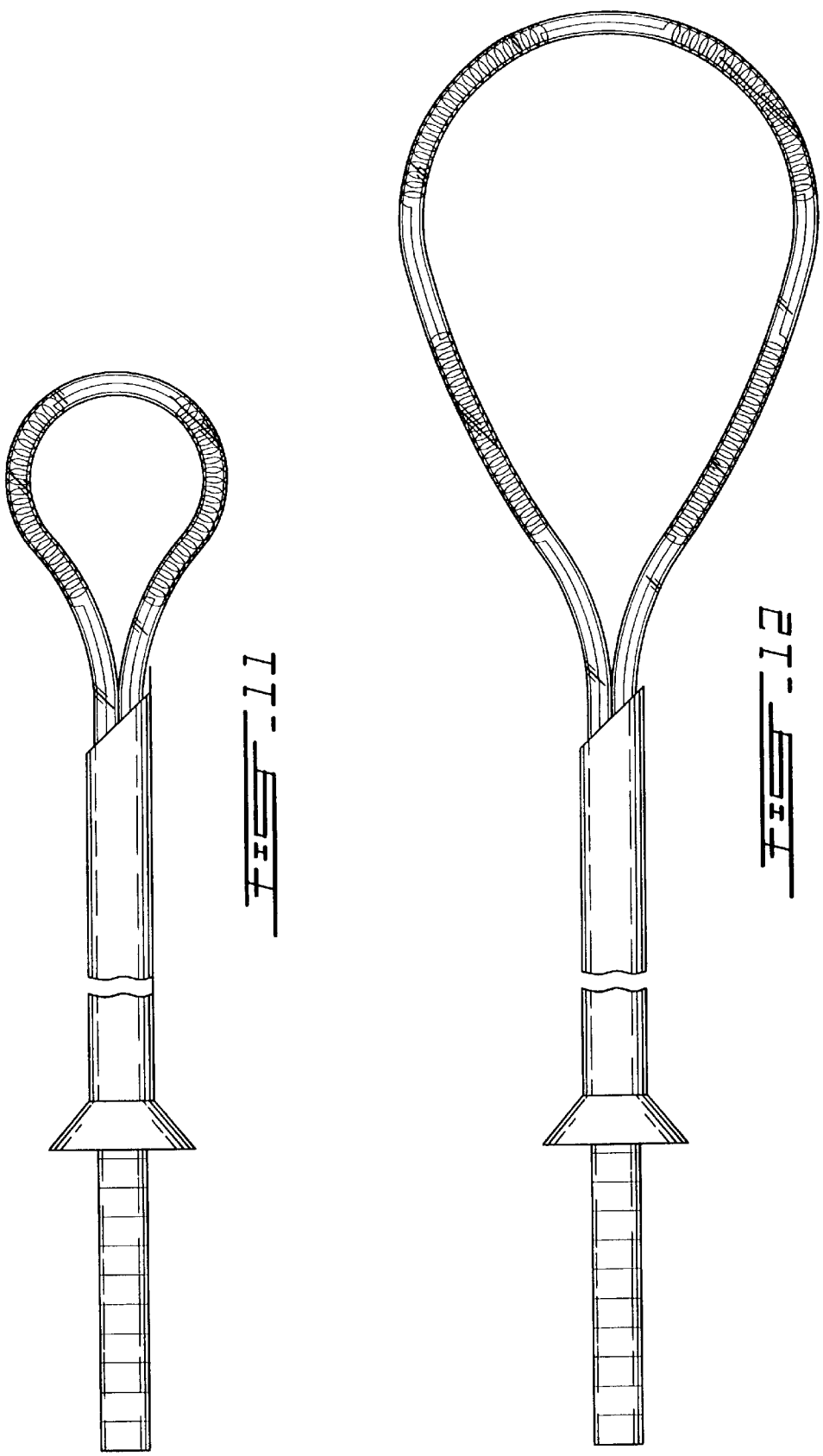

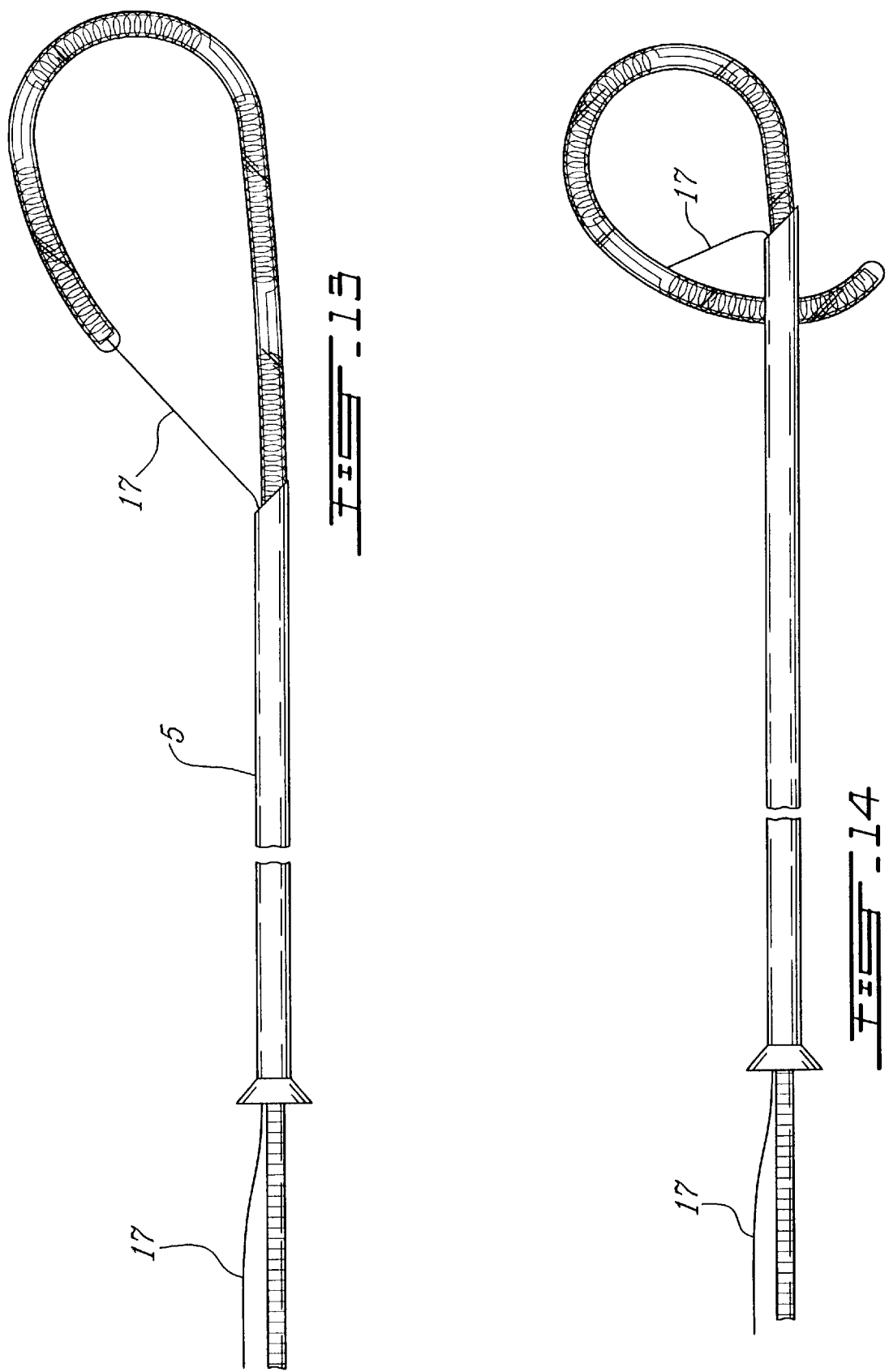

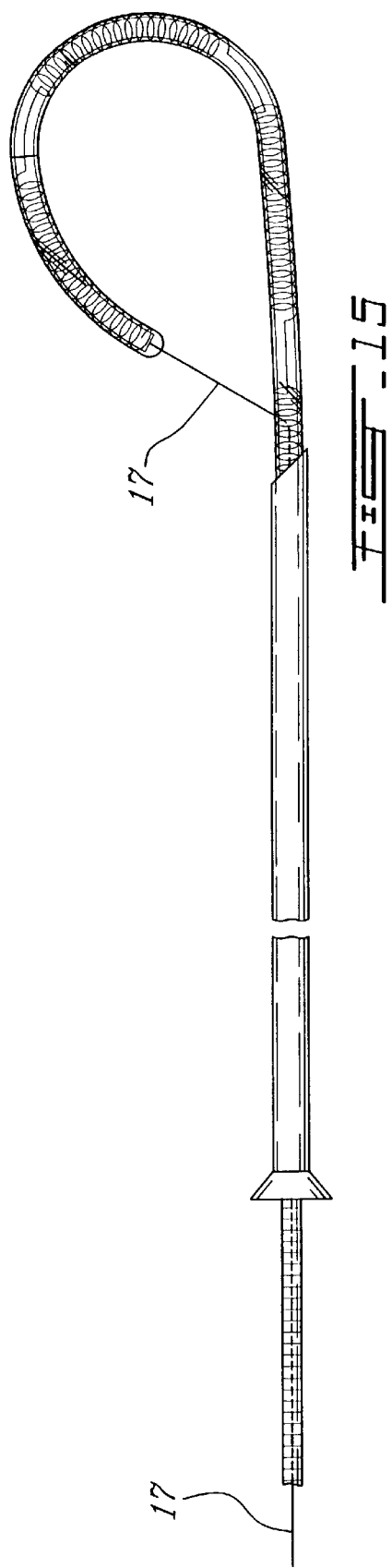

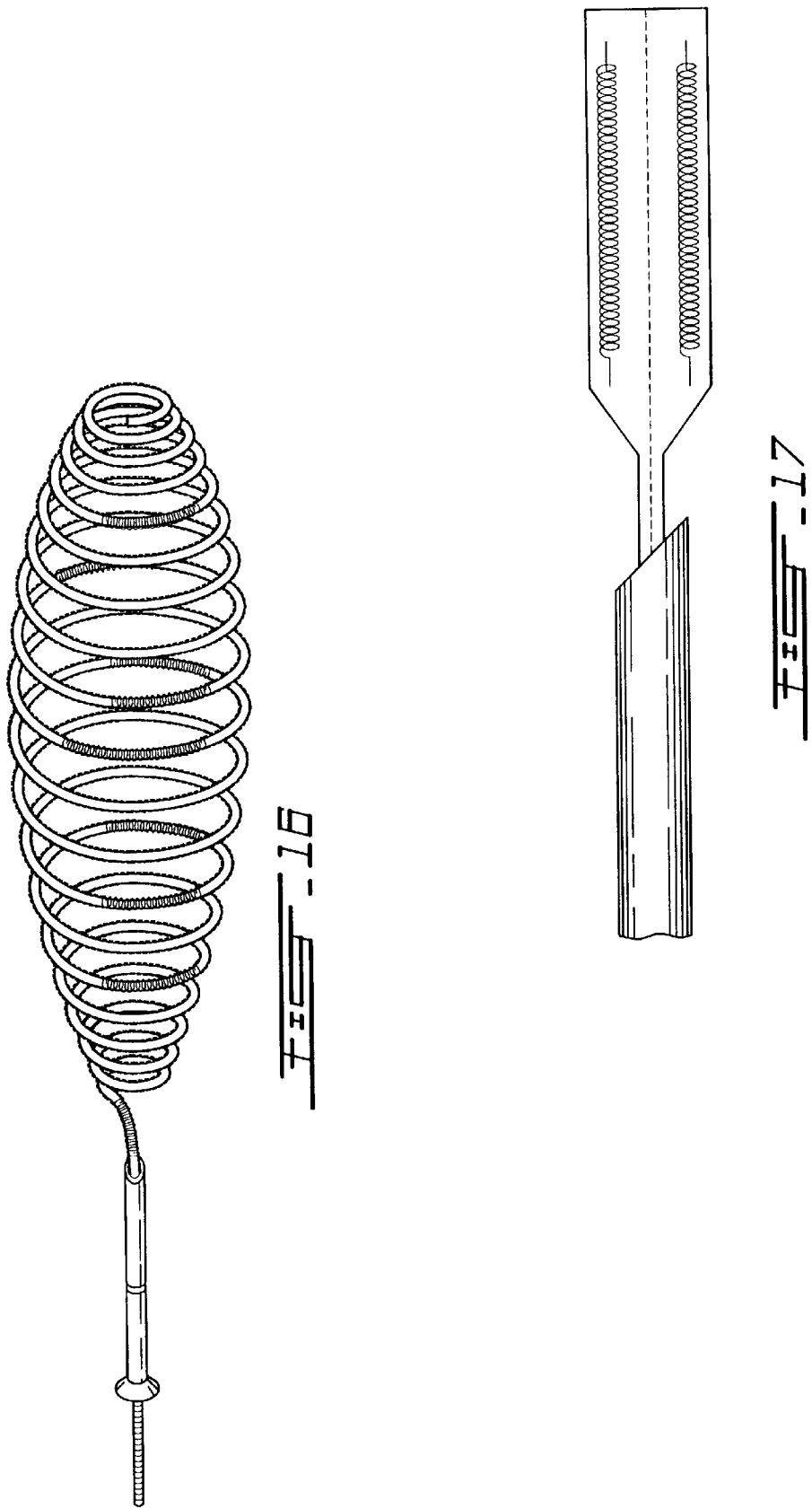

INTRADISCAL LESIONING APPARATUS

TECHNICAL FIELD

The invention relates to an intradiscal lesioning apparatus for treating intervertebral disc disorders, such as localized tears or fissures in the annulus fibrosus, localized disc herniations, and circumferential bulging of discs.

BACKGROUND OF THE ART

Lower back injuries and chronic back pain are a major health problem resulting not only in a debilitating condition for the patient, but consuming a large proportion of funds allocated for health care, social assistance and disability programs. However, there is no consensus among medical researchers on the mechanism of the disorder despite extensive experimentation and clinical testing on the subject. Disc abnormalities may result from trauma, repetitive use in the workplace for example, metabolic disorders or aging.

Each intervertebral disc is composed of a central, gel-like nucleus pulposus surrounded by a tough fibrous semielastic annulus fibrosus. Common disorders include localized tears or fissures in the annulus fibrosus; localized disc herniations with contained or escaped extrusions of the nucleus pulposus; and chronic circumferential bulging of discs. For most patients, however, a well-defined abnormality cannot be found to solely explain the cause of the low back pain, making treatment and pain management very difficult. Isolated cases where a specific anatomic disorder can be diagnosed are the exception. Regrettably, most patients are merely treated symptomatically to reduce pain, rather than to eliminate the root cause of the condition.

The intervertebral discs form about one-quarter the length of the vertebral column in a healthy adult human. Discs are thickest in the cervical and lumbar regions, where the movements of the vertebral column are greatest. With age the vertebral column, including the intervertebral discs, undergo various morphological and biochemical changes such as dehydration of the discs and concaving vertebral bodies. As a result, the size and configuration of the disc components vary considerably from person to person.

The annulus fibrosus is composed of concentric layers of fibrocartilage, in which the collagen fibers are arranged in parallel strands running obliquely between vertebral bodies. The inclination is reversed in alternate layers thereby crossing over each other obliquely. In children and adolescents, the nucleus pulposus is an amorphous colloidal mass of gelatinous material containing glycosaminoglycans, collagen fibrils, mineral salt, water and cellular elements. The nucleus pulposus is normally under pressure and is contained within an ovoid cavity formed laterally by the annulus fibrosus and bounded by thin plates of hyaline cartilage covering the adjacent vertebrae. The annulus fibrosus is thinner nearer to the posterior than to the anterior margin of the disc, and many disc ruptures occur in the posterior region thereby exerting pressure on the adjacent nerve fibers.

Increasingly however, evidence suggests that the source of back pain in many patients are nerves within the degenerated disc itself, rather than the exertion of pressure on adjacent spinal nerves by a damaged disc. For example, as documented by Jonathan C. Houpt, B A, Edison S. Conner, M D, and Eric W. McFarland in "Experimental Study of Temperature Distributions and Thermal Transport During Radiofrequency Current Therapy of the Intervertebral Disc", Spine. 1996;21(15), 1808–1813, afferent innervation of the outer half of the annulus fibrosus has been established whereas the nucleus pulposus contains no nerves or blood vessels. Pain response has been widely reported in response to specific stimulation of the outer layers of the annulus fibrosus. In another study documented by A. J. Freemont, "Nerve ingrowth into diseased intervertebral disc in chronic back pain", The Lancet. 1997; 350, 178–181, nociceptive nerves were found ingrown deeper into the disc, as far as the nucleus pulposus, in association with disc degeneration.

Where patients are diagnosed with clear discogenic pain (i.e. pain originating from a disc), complete surgical removal of the intervertebral disc and fusion of the adjacent vertebrae is often carried out with success rates over 80% in measurable pain reduction after surgery. Such major surgical procedures are invasive, expensive and involve significant risk. To alleviate some of the disadvantages of diskectomy, U.S. Pat. No. 5,201,729 to Hertzmann et al describes a percutaneous method of diskectomy.

Due to the pain reduction success of surgical diskectomy, less drastic means of denervating rather than surgically removing the disc are of significant interest. Denervating the disc is less invasive, less costly, simpler to administer and does not require the fusing of adjacent vertebrae thereby better preserving the patient's freedom of movement.

To destroy nerve cells in the annulus fibrosus, the prior art includes probes that emit various forms of energy from within the nucleus pulposus such as, radio frequency electric current, microwave or thermal energy. It appears that the surface of the disc is devoid of temperature sensing neurological structures, probably since the disc is at core body temperature, and only mechanical and chemical stimulus-sensing nociceptors exist in the annulus fibrosus.

U.S. Pat. No. 5,433,739 to Sluijter et al describes a method of relieving back pain through percutaneous insertion of a needle or electrode into the intervertebral disc under fluoroscopy or other imaging control. Radio frequency electrodes of the same type are commonly used in neurosurgery, anesthesiology and cardiology to lesion neural tissue including an insulated shaft with an exposed tip conducting radio frequency current. A second dispersive electrode with large surface area is placed elsewhere on the patient's body to complete the circuit. The intensity of radio frequency current at the exposed tip causes heating of the adjacent tissue and when the temperature increases sufficiently, the neural tissue is coagulated. The mechanism is direct interruption of the nerves by formation of a lesion and thus the transmissions of pain signals are blocked.

It is well known to those skilled in the art that percutaneous access to the disc is by placing a needle or tube into the disc from the posterior lateral approach, but the limited access does not allow much room to manoeuvre. Once the tube pierces the tough annulus fibrosus, the tube is fixed and has very little freedom of movement. Thus, with a simple needle or electrode, access to only small portions of the central and anterior nucleus pulposus is available.

To permit percutaneous access to the posterior half of the nucleus or to the posterior wall of the disc, U.S. Pat. Nos. 6,007,570; 6,073,051; 6,122,549 and 6,126,682 to Sharkey et al describe a flexible heating element that is inserted into the nucleus pulposus through a hollow tube that has been pierced through the annulus fibrosus. The flexible heating element has sufficient rigidity to be advanced longitudinally under force through the nucleus pulposus while having flexibility to be compliant to the inner wall of the annulus fibrosus. The heating element is guided by sliding contact with the inner wall and ideally should not puncture or damage the annulus fibrosus during positioning.

The shape, size and configuration of the nucleus pulposus may vary considerably and obstacles such as a radial fissure or a fibrous lump, commonly existing in degenerated discs, may impede sliding contact of the heating element. As a person ages, the border between the nucleus pulposus and the annulus fibrosus becomes less distinguished, beginning when a person is about 30 years old. The transition zone is made of both fibrous material of the annulus fibrosus and gelatinous material of the nucleus pulposus. However, the Sharkey heating element relies on sliding contact with the inner wall of the annulus fibrosus to guide it into position and to bend the element into a configuration that closely engages the inner wall of the annulus fibrosus. As a result, the accuracy with which the Sharkey heating element can be placed is limited. Placement may be impeded by damage to the inner wall, ruptures or lack of wall rigidity.

The efficacy of the heat induced denervation procedure appears to depend largely on the accuracy with which energy is applied to the neural tissue within the outer portion of the annulus fibrosus. In Jonathan C. Houpt, B A, Edison S. Conner, M D, and Eric W. McFarland in "Experimental Study of Temperature Distributions and Thermal Transport During Radiofrequency Current Therapy of the Intervertebral Disc", Spine. 1996;21(15), 1808–1813, temperature distribution inside an intervertebral disc and the thermal diffusivity was investigated experimentally. In particular, the temperatures reached in the outer annulus were of interest since this is the area of the disc known to be innervated. The objective of the experiment was to test the hypothesis that back pain relief was due to heat conducting from the centre of the disc to the outer annulus that coagulated the neural tissue or afferent nociceptors therein.

It was found that, under the experimental parameters, clinical intradiscal heating profiles in use did not produce sufficient temperature increases to achieve denervation, and other explanations for the perceived back pain relief were suggested. Heat alone does not appear to explain the clinical results. Nevertheless, the clinical evidence does suggest that there is a clear benefit for many patients who undergo intradiscal treatment, despite the lack of understanding as to the precise cause or mechanism for such improvement in pain relief.

Therefore delivery of various forms of energy to the nucleus pulposus to relieve back pain, preferably immediately adjacent the externally innervated annulus fibrosus, shows promise and will continue to be investigated in the future.

It is an object of the present invention to provide a device that delivers sufficient energy to the annulus fibrosus to achieve denervation and/or modification of collagen fibrils with predicable accuracy.

It is a further objective of the present invention to provide a device that can be accurately positioned, within any portion of the nucleus pulposus of any lumbar intervertebral disc having variable shape, in order to deliver energy to any selected area of the annulus fibrosus.

It is a further object of the invention to provide a device that can adopt a variety of different configurations within the nucleus pulposus to deliver targeted energy to any selected area of the annulus fibrosus.

It is a further object of the invention to provide a heating or energy delivering element that can be positioned in close proximity to the inner wall of the annulus fibrosus, but that does not entirely depend on physical contact with the inner wall of the annulus fibrosus to enable the element to adopt a selected configuration.

Further objects of the invention will be apparent from review of the disclosure, drawings and description of the invention below.

DISCLOSURE OF THE INVENTION

The invention provides an intradiscal lesioning device for percutaneous treatment of a patient's intervertebral disc that has a pathological condition that causes discogenic pain. An elongate introducer having a longitudinal hollow bore is surgically inserted from the patient's skin to extend through the annulus fibrosus thereby providing external surgical access to the nucleus pulposus through the introducer bore. An elongate probe slides through and flexibly conforms to the bore when longitudinally inserted through the bore of the introducer. The distal portion of the probe is capable of conforming to the bore in a longitudinally slidably confined configuration and being deployed into a predetermined configuration when released within the nucleus pulposus in which the distal portion forms at least one loop of a dimension able to remain within the nucleus pulposus without contacting the inner wall. The distal portion houses lesioning devices for emitting energy in the disc when the distal portion is in the deployed configuration. Examples of suitable energy sources include: thermal energy; radio frequency electric current; microwave emission; ultrasound emission; radioactive emission; and optical emission. The deployed preform shape includes: a hook; a spiral coil; a helical coil; a cylindrical coil; a flat plate; an arcuate sheet; an elongate tape; a closed loop; an open loop; and a partial spherical basket.

As well, active actuators may be included for progressively developing the trajectory of the distal portion in three-dimensional space, as the distal portion is longitudinally slidably released from the outer end of the introducer into the nucleus pulposus. For example, mechanical activators can include: a cable extending from the distal end through the introducer; hydraulic actuators within the distal end; piezoelectric actuators within the distal end; and solenoid actuators within the distal end.

Therefore, the system comprises an introducer, a probe that enters the nucleus pulposus via the introducer, an intradiscal distal portion of the probe that resiliently rebounds to a shape that will give close access to the interior wall of the annulus fibrosus, an energy emission device within the distal portion that is supplied by a power source, temperature sensors and a monitoring system that measures temperature and controls the supply of energy.

The introducer is an insertional apparatus that provides proximity to the intervertebral disc. The outer end of the introducer may be sharply beveled to facilitate percutaneous entry and passage through various tissues to reach the intervertebral disc and penetrate the tough, cartilaginous annulus fibrosus. The introducer may also have a stopper or handle on the inner end. In its simplest form, the introducer can consist of a hollow needle-like device, optionally fitted with an internal removable obturator or trocar to prevent clogging during initial insertion. The hollow tube acts as a guide for introducing the instrumentation probe. More complex variations can include one or more temperature transducers, such as thermocouples or thermistors, at various locations along the length of the introducer with exposure to the outer surface of the probe for the purpose of measuring or monitoring the temperature at various locations within the intervertebral disc and surrounding tissue.

For one embodiment, the introducer cross-sectional size is sufficient to house the operational components of the probe while being as small as possible to be minimally invasive. For example, the introducer may be of needle gauge in the range of 18 GA to 15 GA with an outer diameter in the range of 1.283 mm to 1.842 mm and an inner diameter in the range of 0.75 mm to 1.61 mm. The length of the tube is sufficient to reach the intradiscal space from the exterior of a large human posterior-laterally at an angle of 25 to 50° lateral of the midsagittal plane, namely, in the range of 7 cm to 20 cm. The part of the introducer that comes into contact with any internal tissue of the patient is made of biocompatible and sterilizeable material, such as surgical steel. The introducer has sufficient strength to sustain the action of piercing through tissues, notably the cartilaginous annulus fibrosus, to access the nucleus pulposus, various movements within the tissues such as moderate twisting and wiggling, and removal from the tissues.

The probe consists of a proximal end connected to a distal end. The proximal end preferably includes an extension shaft that is stiff and strong enough to allow the user to apply longitudinal force to push the distal end out of the distal end of the introducer and into the nucleus pulposus. The extension shaft can be a tube of 304 stainless steel, optionally with a sheath covering. The outside diameter of the probe extension shaft will range from 0.7 mm to 1.5 mm, the wall thickness will range from 0.05 mm to 0.15 mm and the inside diameter will range from 0.4 mm to 1.4 mm. The length of the extension shaft will be approximately the same length as the introducer, in the range of 7 to 20 cm. Wires to connect the energy source to the delivery mechanism and to connect the temperature sensors in the probe to the monitoring system can pass through the extension shaft.

The distal end of the probe, or intradiscal portion, will be flexible enough to take a shape that allows close proximity with the inner wall of the annulus fibrosus. The probe distal portion passively and resiliently rebounds to a preform shape to actively navigate through the nucleus pulposus. The distal portion shape includes but is not limited to a shape memory alloy loop, coil, basket, or manually extended loop and can be navigated using electronic, mechanical or hydraulic means. The distal portion will also carry the components that supply thermal energy, temperature sensors or other means of denervating the annulus fibrosus with energy emissions under controlled conditions.

Therefore it will be appreciated that the invention provides significant advantages over the prior art specifically U.S. Pat. Nos. 5,980,504 and 6,007,570 to Sharkey et al. The flexible heating element of the Sharkey patents is dependent on engaging inner wall of the annulus fibrosus and is guided by sliding contact with the inner wall to form the curved shape within the nucleus pulposus. Since many damaged portions of an intervertebral disc require treatment of the posterior section of the disc, reliance on contact with the inner wall significantly limits the ability of the flexible Sharkey heating element to engage the full interior wall of the disc.

In contrast, the present invention provides several preform shapes and actively navigated shapes that can engage any selected target portion or the entire posterior lateral or anterior portions of the inner wall of the annulus fibrosus.

A method for percutaneous treatment of a patient's intervertebral disc is also provided. The method comprises surgically inserting and placing an elongate introducer, comprising a tube having an inner end, an outer end and a longitudinal hollow bore extending therebetween through the annulus fibrosus thereby providing external surgical access to the nucleus pulposus through the bore; inserting an elongate probe having a proximal portion and a distal portion into the bore, the probe slidably engaging and flexibly conforming to the bore when longitudinally inserted through the bore from the inner end to the outer end of the introducer; deploying a distal portion of the probe into a configuration within the nucleus pulposus in which the distal portion forms at least one loop of a dimension able to remain within the nucleus pulposus without depending on contact with the inner wall; connecting the probe to an energy source; and emitting energy from the energy source at the distal portion into the disc.

Further advantages of the invention will be apparent from the following detailed description and accompanying drawings.

DESCRIPTION OF THE DRAWING

In order that the invention may be readily understood, embodiments of the invention are illustrated by way of example in the accompanying drawings.

FIG. 2 is a sectional view through an intervertebral disc along lines 2, 2 of FIG. 1 also showing insertion of the introducer with probe initially entering the nucleus pulposus.

FIG. 3 is a detailed view of the introducer with probe fully inserted to illustrate the coil loop pre-form shape of this embodiment when allowed to freely rebound to its unconstrained configuration.

FIG. 4 is a further detailed view of the coil loop embodiment illustrated in FIG. 3 showing the helical resistant heat emitting elements within the coiled distal portion of the probe.

FIG. 5 is a detailed view of one embodiment of the probe showing longitudinal electrical wires connected to two separate helical thermal heating elements with elongate temperature sensors housed within a transparent flexible plastic casing.

FIG. 6 is a like detailed view of the distal portion of the probe, however, showing a central flexible metal core in dashed outline with two layers of external sheaths for electrical insulation and heat transfer capability.

FIG. 7 shows a second embodiment of the invention wherein the pre-formed shape is a single open loop to enable the distal portion of the probe to be positioned within the nucleus pulposus adjacent the posterior of the inner wall (see FIG. 22).

FIG. 8 is a third embodiment illustrating a pre-form shape as a closed loop with hooked end.

FIGS. 9, 10, 11 and 12 show deployment steps for a fourth embodiment with preformed shape as an axially symmetric closed loop.

FIG. 9 is the first step of deployment of the fourth embodiment wherein the extension shaft of the probe has been extended slightly outwardly of the outer end of the introducer.

FIG. 10 shows the fourth embodiment of FIG. 9 wherein the extension shaft of the probe has been extended further outwardly of the outer end of the introducer and wherein the loop has a shape modified because of the pressure exerted on it by the inner wall, for example.

FIG. 11 shows the fourth embodiment of the FIG. 10 wherein the extension shaft of the probe has been extended further outwardly of the outer end of the introducer and wherein the loop has penetrated through the inner wall and into the fibrosus and is reaching its preform shape.

FIG. 12 shows the fourth embodiment of the FIG. 11 wherein the extension shaft of the probe has been extended further outwardly of the outer end of the introducer and wherein the loop has deployed fully into the disc.

FIG. 13 shows a fifth embodiment of the invention with a pre-form in the shape of a semi-closed loop with active shape controlling cable attached to the extreme distal end of the probe and extending through the introducer enabling the surgeon to actively control the shape of the distal portion.

FIG. 14 shows the fifth embodiment of the invention with cable secured from the tip of the probe in order to fold the probe distal portion over into an open loop shape.

FIG. 15 shows the fifth embodiment with cable passing into the interior of the probe in contrast to passing the cable externally of the probe as in FIG. 13.

FIG. 16 shows a sixth embodiment of the invention wherein the pre-form shape is a helicoidal coil loop that collapses to withdraw through the introducer once the procedure has been completed.

FIG. 17 shows a seventh embodiment of the invention wherein the pre-form shape is a flat plate, arcuate sheet or elongate tape depending on the length and lateral flexibility of the distal end of the probe, wherein the heating elements are arranged to form a closed, semi-closed or open loop and showing beveled rearward edges that serve to roll or fold the distal end of the probe when retracted through the introducer.

Further details of the invention and its advantages will be apparent from the detailed description included below.

DETAILED DESCRIPTION OF PREFERRED EMBODIMENTS

Figure 1:
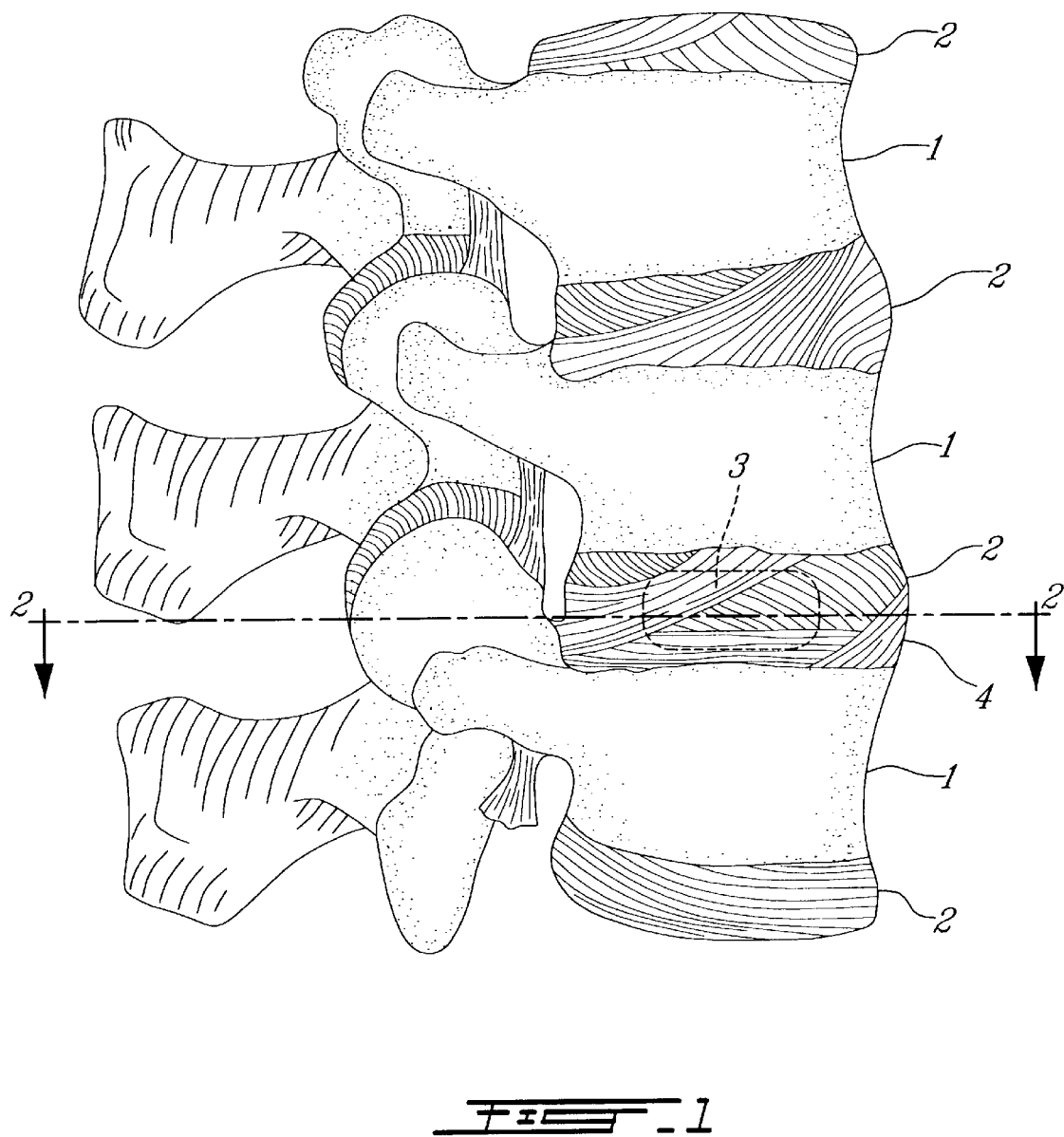
FIG. 1 is a lateral view of three human vertebrae with intervertebral discs illustrated and showing the nucleus pulposus in dashed outline.

FIG. 1 shows a lateral view of three human vertebrae 1 with intervertebral disc 2 between each vertebra 1. As drawn the posterior is toward the left and anterior towards the right. With reference to FIG. 2, the vertebral disc 2 comprises two main structures with a central gelatinous nucleus pulposus 3 bounded by a tough annulus fibrosus 4. As indicated in FIG. 1, the annulus fibrosus 4 has a number of overlapping layers which are obliquely oriented spanning between the adjacent vertebra 1 in opposing overlapping orientations.

As shown in FIG. 2, the intradiscal lesioning device includes an elongate introducer 5 having an inner beveled end inserted within the nucleus pulposus and an outer end which extends outwardly of the patient's body. A longitudinal hollow bore extends through the tube 5 and provides for percutaneous surgical insertion of the tube 5 through the annulus fibrosus 4 thereby providing external surgical access to the nucleus pulposus 3 through the bore.

Once the surgeon has accurately located the elongate introducer by means of fluoroscopy or other imaging systems, the elongate probe 6 is pushed through to slidably engage and flexibly conform to the bore of the introducer 5. The proximal portion 7 of the probe 6 includes a handle and control means as well as markings 8 to visually indicate the extent of insertion of the probe 6. The distal portion 9 of the probe 6 is shown in FIG. 2 initially being longitudinally pushed out of the outer end of the introducer 5 into the soft gelatinous nucleus pulposus 3. Depending on the selected preform shape of the distal portion (various examples of which are shown in FIGS. 4, 7 through 18) selected portions or the entire inner wall of the annulus fibrosus 4 can be engaged.

For example, as shown in FIGS. 3 and 4, the distal portion 9 may be pre-formed into a spiral coil shape to resiliently rebound to a spiral deployed configuration when released within the nucleus pulposus 3 while remaining capable of resiliently conforming to the bore within the tube 5 in a longitudinally slidable confined configuration therein.

The distal portion 9 can include passive or active means to change its shape once inserted into the nucleus pulposus 3. Passive shape biasing means to resiliently urge the distal portion 9 to adopt a selected pre-form shape, such as in FIG. 4 a spiral coil shape. Such passive shape biasing means can be constructed of various resilient materials such as shape memory metallic alloy, super elastic surgical rubber, resilient plastic and even natural rubber. For example, as shown in FIG. 6 a resilient solid fiber core 10 and resilient outer tubes 11 and 12 can be provided depending on the necessary insulation and physical properties required. Resilient fibers may also be woven in tubular shapes as in electrical co-axial cables or in an annular array of longitudinal resilient fibers or in a resilient protective sheet. Alternatively as shown in FIG. 5 the entire probe may be molded as a solid plastic unit with embedded heating coils and control means. The passive shape biasing means can also be a resilient tube, a woven tube of resilient fibers, an annular array of longitudinal resilient fibers, or a resilient sheath.

As indicated in FIGS. 5 and 6 the distal portion 9 of the probe 6 includes lesioning means for emitting energy toward the inner wall of the annulus fibrosus 4 when the distal portion 9 is in its deployed configuration (for example see FIGS. 20 through 23). In the embodiment illustrated in FIGS. 5 and 6, the lesioning means comprise helical electrically powered heating coils 13.

In the embodiments illustrated, the coils 13 are individually controllable with separate electrical supply conduits 14 longitudinally through the length of the probe 6. The probe 6 may also contain various monitors such as a thermometer, thermistor, thermocouples or ammeters illustrated in FIGS. 5 and 6 as housed within a conduit 15. If necessary, as shown in FIG. 5 further structural or resilient strength can be provided by a separate mounting wire 16. It will be understood that the invention is not restricted to any particular lesioning means. It is intended that the lesioning means may include any energy emitting device which may be of therapeutic use within the nucleus pulposus 3 such as thermal energy coils, radio frequency electric current, ammeters, microwave ammeters, ultrasound ammeters, radio active emission devices or optical emission devices.

The intradiscal lesioning device may be designed to passively or actively adopt any number of deployed configurations. Various deployed configurations are required due to the various shapes of the nucleus pulposus 3, various sizes depending on the location of the injured intervertebral disc 2, depending on the age of the patient, the clarity of definition between the nucleus pulposus and the annulus fibrosus 4 and depending on the extent of damage or rupture in the disc itself. Whereas FIGS. 3 and 4 show an embodiment taking the pre-form shape of a spiral coil, FIG. 7 shows a pre-form shape of a simple overlapping open loop. FIG. 8 shows a device pre-formed into a hook shape with dual strands in a closed loop, however, it will be understood that a single strand hook shape can be provided by the embodiment shown in FIG. 7.

Figure 18:
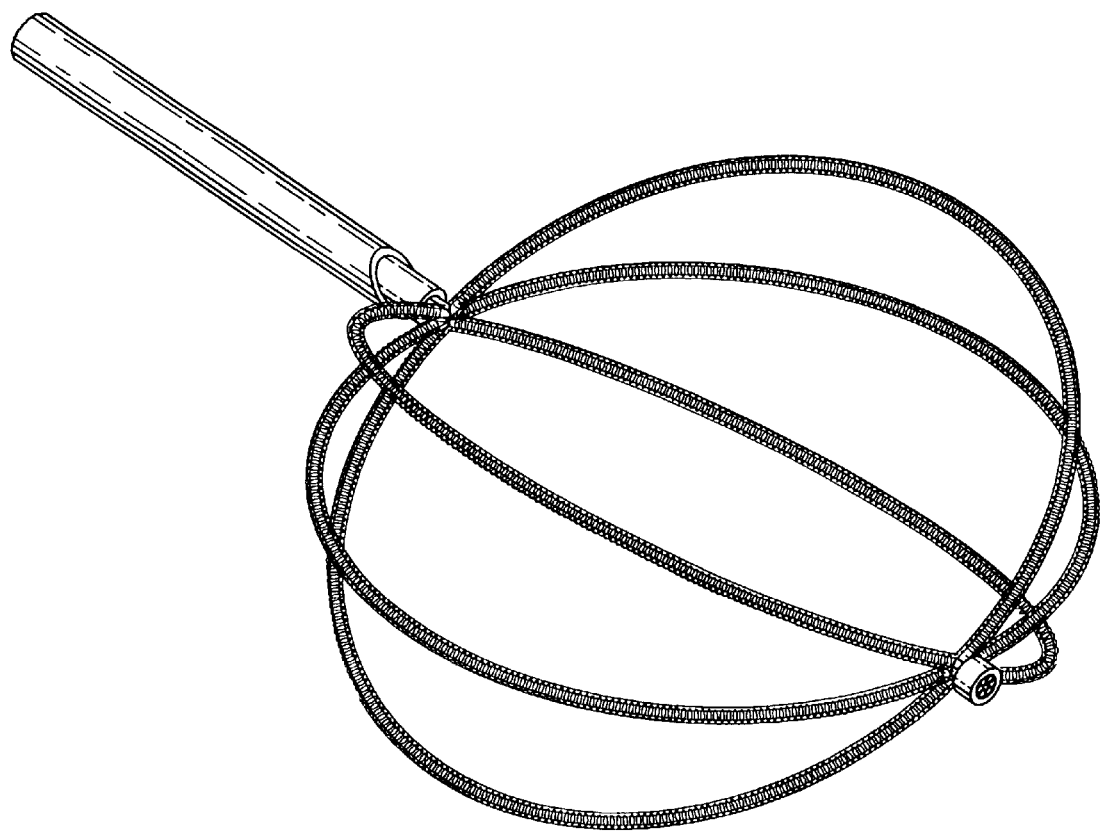
FIG. 18 is an eighth embodiment of the invention showing a pre-form shape of a partial spherical loop basket with six arcuate loop strands extending between outer and inner poles disposed longitudinally and being flexible enough to retract within the introducer when withdrawn.
Figure 19:
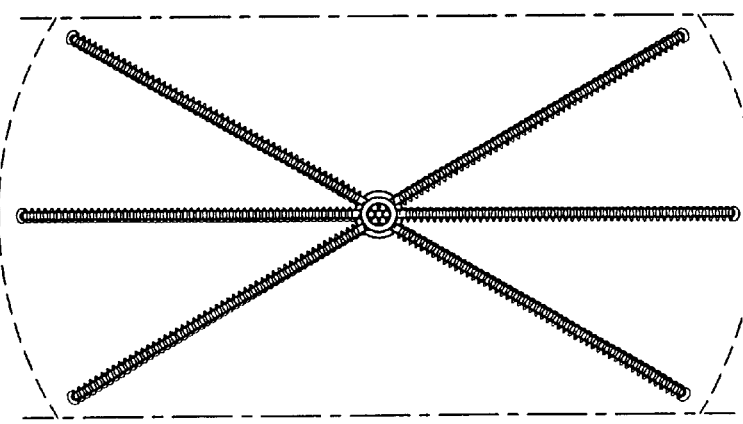
FIG. 19 shows the eighth embodiment of FIG. 18 in an end view to indicate in dashed outline the ability of this embodiment to completely engage the inner wall of the annulus fibrosus.
Figure 20:
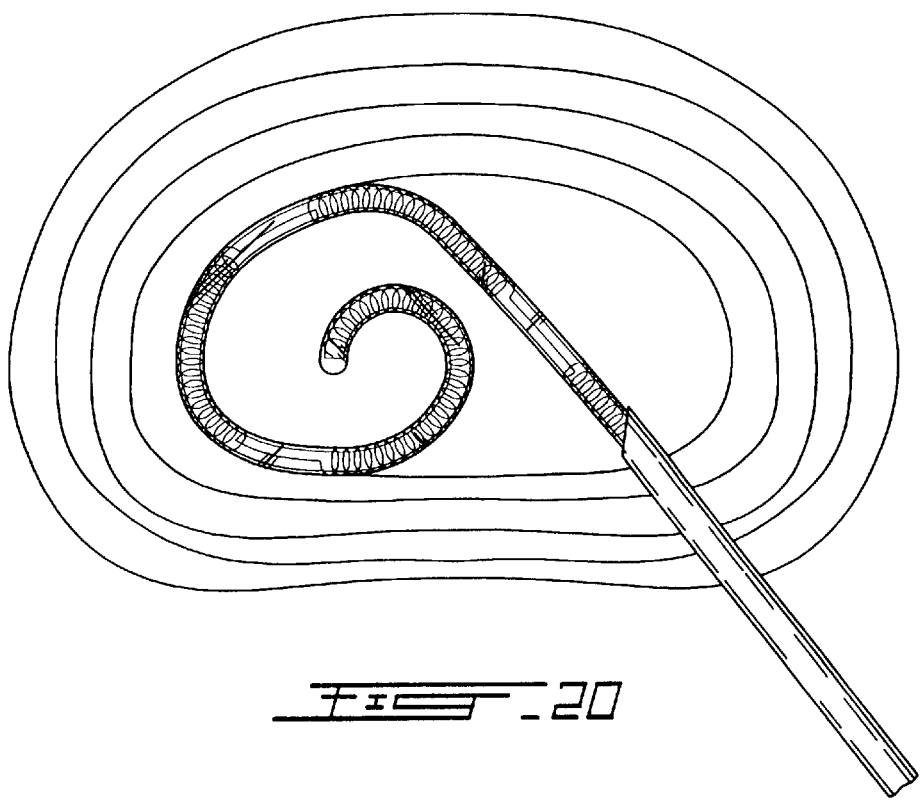
FIG. 20 is a sectional view through an intervertebral disc showing insertion of the spiral coil loop embodiment that is shown in FIGS. 3 and 4.
Figure 21:
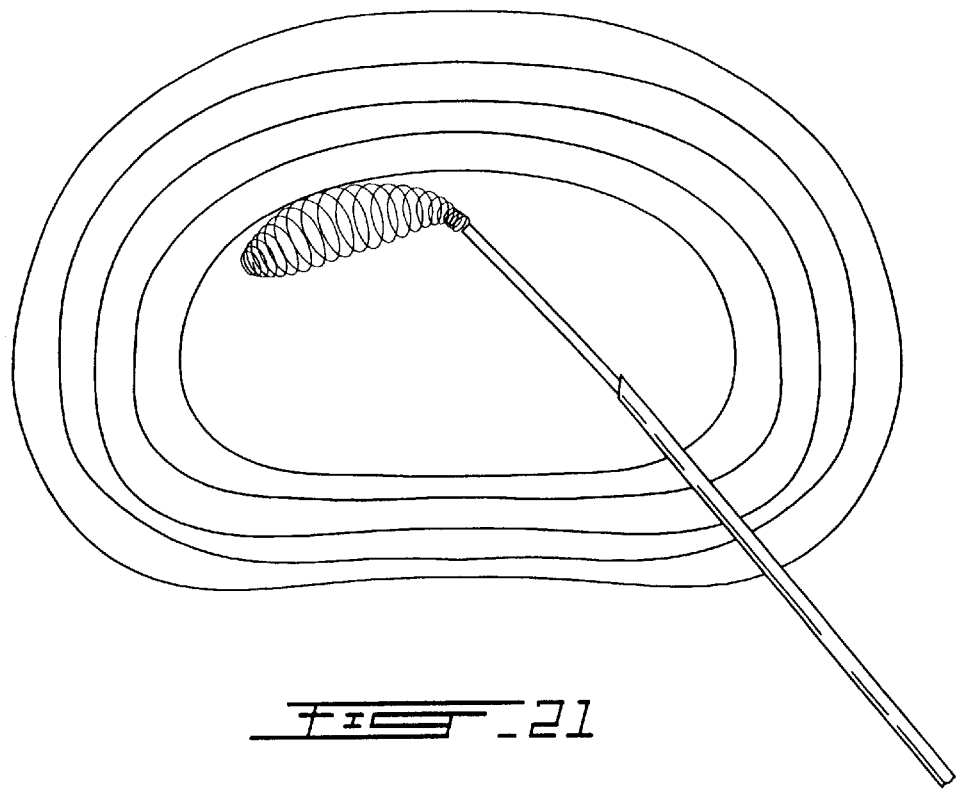
FIG. 21 is a like sectional view showing the deployed configuration of the embodiment illustrated in FIG. 16.
Figure 22:
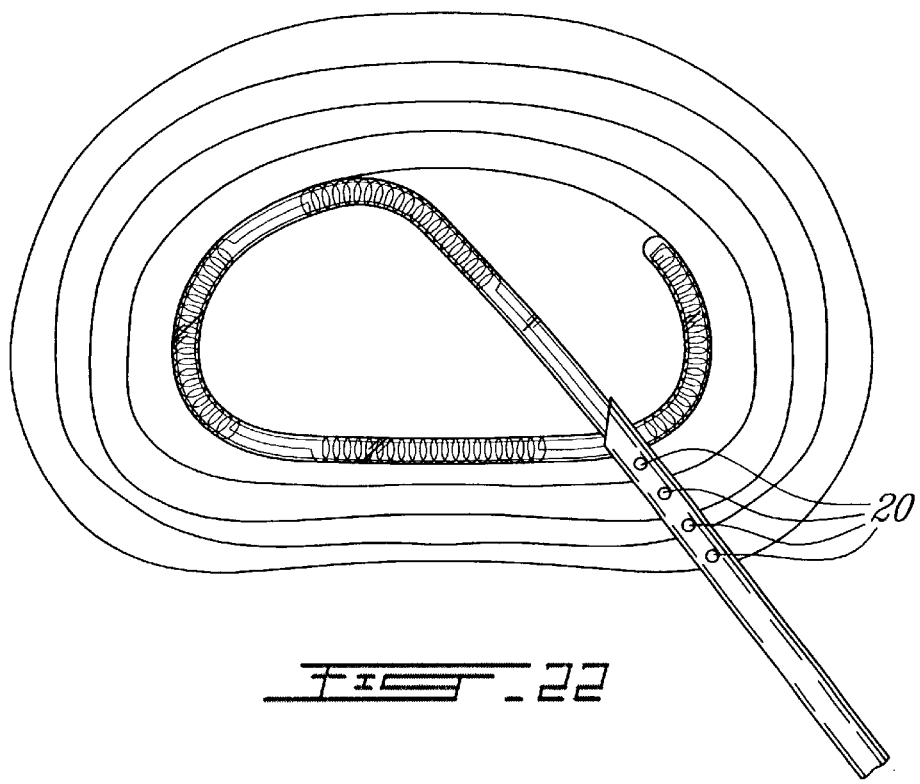
FIG. 22 is a like sectional view showing the deployed position of the embodiment illustrated in FIG. 7.
Figure 23:
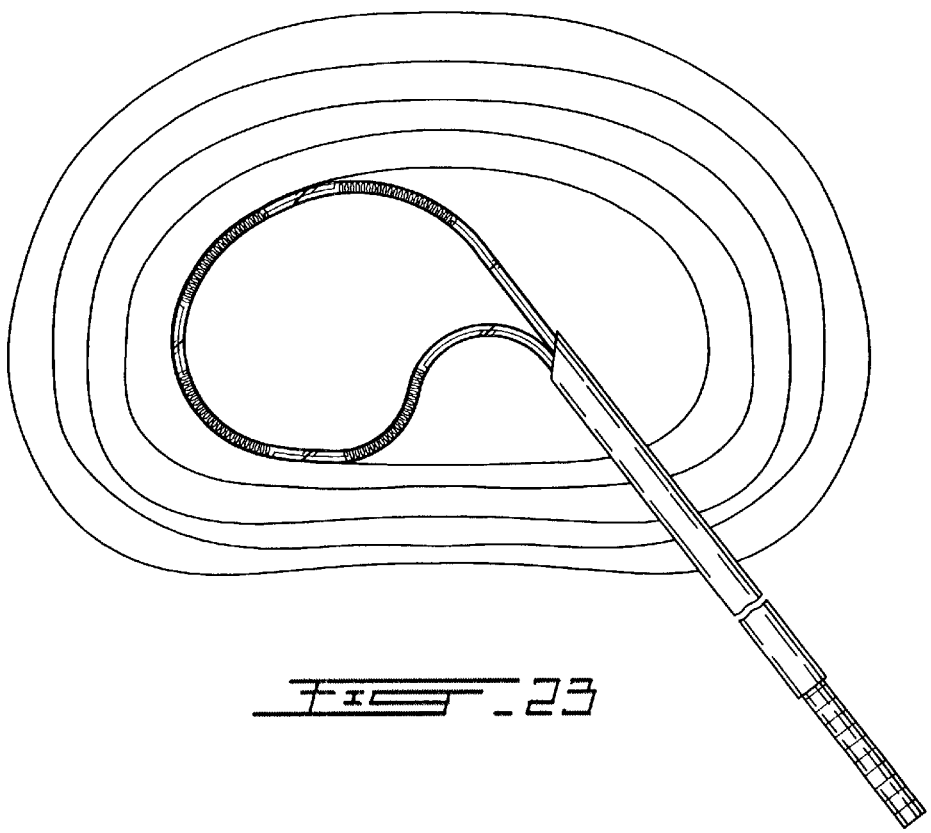
FIG. 23 is like sectional view showing the deployed configuration of the embodiment illustrated in FIG. 12.

FIGS. 9, 10, 11 and 12 show the deployment of dual strand closed loops as they are being pushed out of the probe and as they attain their preform shape. FIG. 16 shows a helical coil having varying diameter longitudinally, however, it will be understood that a coil of cylindrical shape or alternating diameter can be easily constructed. In a like manner, FIG. 17 shows a relatively short flat plate configuration, however, it will be understood that an arcuate sheet or elongate tape may also be constructed in a like manner. As indicated in FIGS. 18 and 19 complex shapes of multiple strands can also be constructed provided that they are weak enough to collapse within the bore of the introducer when inserted and withdrawn from the nucleus pulposus while being rigid enough to be pushed longitudinally through the introducer into the nucleus pulposus. An advantage of the embodiment shown in FIGS. 18 and 19 is the complete coverage of the interior wall of the annulus fibrosus with multiple strands which expand once installed.

Referring to FIGS. 13, 14 and 15, the lesioning device may also include active shape control means for progressively developing the trajectory of the distal portion 9 in three dimensional space as the distal portion is longitudinally slidably released from the outer end of the introducer 5 into the nucleus pulposus 3. In the embodiment shown, the active shape control means is a cable that extends from the distal end through the introducer 5. In the case of FIG. 13 the cable 17 extends from the extreme distal end of the probe through the introducer 5. In the case of the embodiment shown in FIG. 14 the cable 17 is secured to the probe longitudinally spaced from the extreme distal end in order to enable the probe to fold over itself into an open loop.

FIG. 15 shows a further example of use of a cable that is threaded through the interior of the probe as opposed to extending parallel with the probe itself. It will be appreciated that other mechanical activators are within the scope of the invention such as hydraulic actuators within the distal end, piezo-electric actuators or solenoid actuators. In all cases the actuators will serve to actively control the shape of the distal portion as it is released from the outer end of the introducer and is pushed through the nucleus pulposus.

By providing a pre-selected pre-form shape or by actively controlling the shape of the distal portion as it is pushed through the nucleus pulposus, the invention provides means to control the shape, location and positioning of energy emitting devices within the distal portion of the probe thereby providing significant advantage over the prior art which relies on contact and sliding guidance of the distal end of the probe as it contacts the inner wall of the annulus fibrosus. Superior control over the shape and positioning of the distal portion serves to better locate and control the emission of thermal energy or other forms of energy to denervate the annulus fibrosus.

Figure 24:
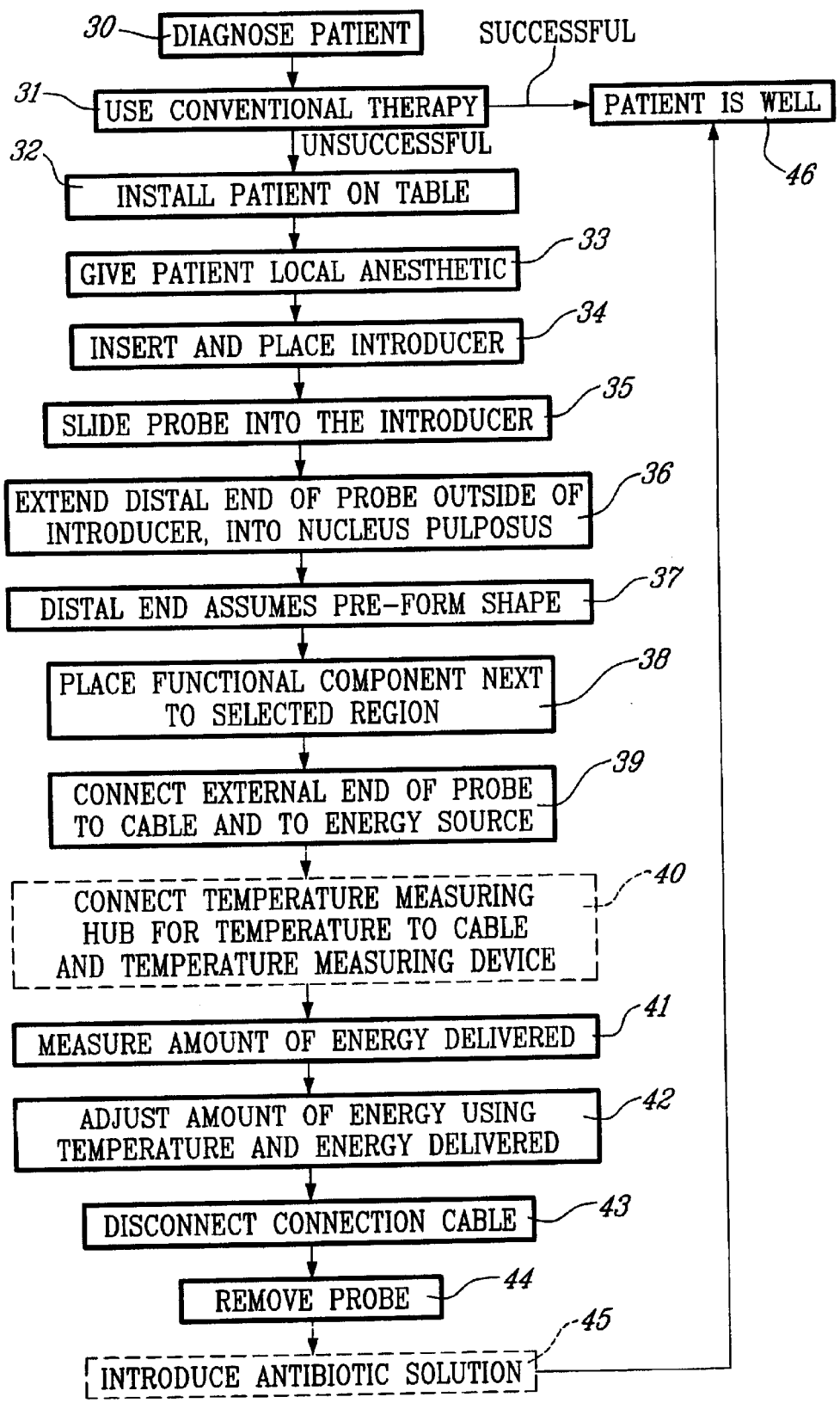

The method for treating a condition of the intervertebral disc with an intradiscal lesioning apparatus according to the invention utilizes the apparatus of the invention to modify the tissue at a selected location of the intervertebral disc. With reference to FIG. 24, the patient is first diagnosed 30 using a number of methods to determine the condition of the disc. Examples of current diagnostic methods include discography, MRI and CT. An evaluation of the intensity of pain may also be used. If the disc shows signs of internal disruption, degeneration or non-protruding herniation the doctor may decide that the pain experienced is originating from the disc. If conventional therapy such as a combination of rest and physiotherapy is unsuccessful 31 a decision can be made to have the intradiscal therapy. The patient lies on the operating table in the prone position and the area of the back to be treated is cleaned, disinfected and draped 32. A local anesthetic 33 is administered to the area that is to be treated and the patient may be put under a mild sedative. It is important that the patient be conscious during the procedure to provide feedback to the practitioner to avoid damage of tissues around the disc such as the spinal cord or spinal nerves. An introducer is provided that is used for percutaneous, minimally invasive access to the disc. The introducer is a hollow shaft that is inserted through the skin approximately 10 to 15 cm lateral of the spine, travelling through the tissues of the back to the intervertebral disc that is to be treated. A trocar can be used while inserting the introducer to stop tissue or fluid from entering the hollow lumen. Anyone experienced in performing percutaneous intradiscal procedures would be very familiar with the access path to the disc and the tissues that must be avoided. The placement of the introducer is aided by fluoroscopic guidance 34. Once the introducer is placed, the trocar is removed and one opening to the lumen will be external to the body and the other will be inside the nucleus pulposus, entering the disc from the posterolateral angle.

The probe has an end that contains a functional component and the other end has a connection hub that connects the probe to a cable that leads to the energy source. Without connecting the cable to the probe, the probe is then slid into the lumen of the introducer 35, functional component first. Placement of the probe can be aided by fluoroscopy. As the end of the probe containing the functional component is advanced out of the end of the introducer that is in the nucleus pulposus 36, the length of the probe that is out of the introducer will assume its predefined shape 37. The predefined shape is such that the functional component can be placed next to a selected region of the annulus fibrosus 38. Once the functional component is placed in the desired region the probe can be connected to the cable, which in turn is connected to the energy source 39. One of the embodiments (see FIG. 22) has a set of thermocouples imbedded in the introducer. If an introducer is used that contains temperature measuring elements it will have a connection hub on the end that is external to the patient's body. At this time the connection hub is connected to a cable that is connected to a measurement device 40.

The energy source can be controlled by a program that creates a profile of amount of energy delivered 41 and uses the temperature of the disc tissue in a feedback loop. For example, if the form of energy to be used is electricity such as AC electricity or radiofrequency AC electricity to heat a resistive thermal element, one or more temperature sensors can feedback to the power source controller and the desired amount of power can be sent 42 to the resistive thermal element in order to adjust the temperature to reach a setpoint. The temperature profile of functional element would be designed to achieve the following criteria: the temperature at the region of the disc that contains nociceptors that are most likely to be causing discogenic pain is to be raised to at least 45° C. (studies have shown this region to be in the outer third of the annulus); the temperature of the annulus fibrosus in the region of a fissure or disruption can be raised to at least 60° C. in order to constrict the collagen; the temperature must be raised slow enough so as to allow the heat to be dissipated to the outer third of the annulus fibrosus while not elevating the tissue in direct contact to the probe to cause thermal injury such as charring or causing an inflammatory response. Based on these criteria the set-point for application of energy can change (increase, decrease or hold at the same level) according to a set profile.

If there is one feedback component, as in the embodiment that has a temperature-sensing device in the core of the probe, assumptions must be made to meet the criteria of the temperature profile. These assumptions must be carefully justified because if miscalculated the consequences can be inadequate treatment by not raising the temperature enough, or injury from raising the temperature too much. Studies would be done to determine parameters of the profile such as the rate of change of temperature at the measured site and the duration of application to determine the resulting thermal dissipation and the temperature at other sites in the disc. If there is more than one feedback component, as in the embodiment that has a temperature sensor in the core of the probe and at least one in the introducer, effectiveness in meeting the criteria of the temperature profile is increased.

When the energy source is activated to supply energy to the probe's energy applicator, the feedback control system determines the amount of energy delivered in relation to time. During the delivery of energy the patient is asked if any abnormal pain is experienced. This is done as a safeguard against injuring the spinal nerves near the disc.

When the temperature is raised to the desired level and for the desired duration the connection cables can be disconnected 43. As the probe is then slowly removed from the introducer the deployed shape will be retracted through the introducer 44. When the probe is completely removed from the introducer a solution of antibiotic 45 can optionally be injected into the disc using the introducer. The reason for this is to avoid infection. The patient should then start noticing a difference in the pain felt 46.

Although the above description relates to specific preferred embodiments as presently contemplated by the inventors, it will be understood that the invention in its broad aspect includes mechanical and functional equivalents of the elements described herein.

We claim:

1. An intradiscal lesioning device for percutaneous treatment of a patient's intervertebral disc, the disc including a nucleus pulposus bounded by an annulus fibrosus and cartilage endplates, an inner wall of the annulus being defined between the nucleus and the annulus, said device comprising:

an elongate introducer, comprising a tube having an inner end, an outer end and a longitudinal hollow bore extending therebetween, for percutaneous surgical insertion into the annulus fibrosus thereby providing external surgical access to a target region of the disc;

an elongate probe having a proximal portion and a distal portion, the probe slidably engaging in the bore when longitudinally inserted through the bore from the inner to the outer end of the introducer tube;

wherein the distal portion is capable of conforming to the bore in a longitudinally slidably confined configuration therein and being deployed into a configuration when released within the nucleus pulposus in which the distal portion forms at least one loop of a dimension able to remain within the nucleus pulposus without depending on contact with said inner wall; and the distal portion comprising means for emitting energy at a desired location in the disc;

wherein the distal portion includes active shape control means for controlling at least one of a trajectory, a position, a size, a shape and a deployment of the distal portion in three-dimensional space, as the distal portion is longitudinally slidably released from the outer end of the introducer tube into the nucleus pulposus;

wherein a shape of the distal portion differs for a range of lengths of the distal portion being released within the nucleus pulposus;

whereby the distal portion can be forced to take on a preferred shape and trajectory for the percutaneous treatment of the disc.

2. An intradiscal lesioning device according to claim 1 wherein the active shape control means comprises a cable extending from the distal portion through the introducer tube.

3. An intradiscal lesioning device according to claim 1 wherein the means for emitting energy emit resistive heating energy.

4. An intradiscal lesioning device according to claim 1 wherein said providing external surgical access to a target region of the disc comprises providing external surgical access to the nucleus pulposus through said bore.

5. An intradiscal lesioning device according to claim 1, further comprising said elongate introducer having at least one temperature measuring element on said introducer;

a temperature measuring device being electrically connected to said at least one temperature measuring element for measuring a temperature of tissue.

6. An intradiscal lesioning device according to claim 5, further comprising a controller for controlling said lesioning means using said temperature.

7. A method for percutaneous treatment of a patient's intervertebral disc, the disc including a nucleus pulposus bounded by an annulus fibrosus and cartilage endplates, an inner wall of the annulus fibrosus being defined between the nucleus pulposus and the annulus fibrosus, said method comprising:

surgically inserting and placing an elongate introducer, comprising a tube having an inner end, an outer end and a longitudinal hollow bore extending into the annulus fibrosus thereby providing external surgical access to a target region of the disc;

inserting an elongate probe having a proximal portion and a distal portion into said bore, the probe slidably engaging and flexibly conforming to the bore when longitudinally inserted through the bore from the inner end to the outer end of the introducer tube;

deploying a distal portion of said probe into a configuration within the nucleus pulposus in which the distal portion forms at least one loop of a dimension able to remain within the nucleus pulposus without depending on contact with said inner wall;

controlling at least one of a trajectory, a position, a size, a shape and a deployment of the distal portion in three-dimensional space, as the distal portion is longitudinally slidably released from the outer end of the introducer tube into the nucleus pulposus, wherein a shape of the distal portion differs for a range of lengths of the distal portion being released within the nucleus pulposus and whereby the distal portion can be forced to take on a preferred shape and trajectory for the percutaneous treatment of the disc;

connecting said probe to an energy source; and emitting energy from said energy source at said distal portion to a desired location in the disc.

8. A method according to claim 7 wherein the controlling is done using a cable extending from the distal portion through the introducer tube.

9. A method according to claim 7 wherein said providing external surgical access to a target region of the disc comprises providing external surgical access to the nucleus pulposus through said bore.

10. A method according to claim 7, further comprising measuring a temperature of tissue using at least one temperature measuring element near a distal end of said introducer.

11. A method according to claim 10, further comprising controlling said emitting using said temperature.

* * * * *